United States Patent [19]
Truitt, Jr. et al.

[11] Patent Number: 5,460,970
[45] Date of Patent: Oct. 24, 1995

[54] SEPARATION OF ACETALDEHYDE - INDUCED HEMOGLOBIN (HB $A_{1-ACH}$)

[75] Inventors: Edward B. Truitt, Jr., Kent; Susan E. Hazelett, Mogadore; Robert A. Liebelt, Akron, all of Ohio

[73] Assignee: Summa Health System, Akron, Ohio

[21] Appl. No.: 63,256

[22] Filed: May 18, 1993

[51] Int. Cl.$^6$ .................................................. G01N 33/72
[52] U.S. Cl. .............................. 436/66; 436/67; 436/128; 436/132; 436/161; 422/70
[58] Field of Search ............................. 73/61.52, 61.65; 436/128, 66, 67, 132, 161; 422/70

[56] References Cited

U.S. PATENT DOCUMENTS

| | | | |
|---|---|---|---|
| 4,468,330 | 8/1984 | Kamiyama et al. | 210/656 |
| 4,473,640 | 9/1984 | Combie et al. | 435/18 |
| 4,517,241 | 5/1985 | Alpert | 428/332 |
| 4,777,132 | 10/1988 | Green et al. | 435/25 |
| 4,814,280 | 3/1989 | Peterson | 436/128 |
| 4,837,157 | 6/1989 | Turnell et al. | 436/20 |
| 4,855,054 | 8/1989 | Williams | 210/635 |
| 4,980,058 | 12/1990 | Bruegger | 71/61.52 |

OTHER PUBLICATIONS

Huisman, et al., A new high–performance liquid chromotographic procedure to quantitate hemoglobin $Al_c$, J. Lab Clin Med 102:163–173 (1983).

Peterson, et al., Artefactual Increase in Hemoglobins, Alcoholism: Clin Exp Res 10:219–220 (1986).

Homaidan et al., Acetaldehyde–Hemoglobin Adducts, Clin Chem 30/3, 480–482 (1984).

Sillanaukee, et al., Association of a Haemglobin–Acetaldehyde Adduct with Questionnaire Results on Heavy Drinkers, Alcohol 26: 519–525 (1991).

Sillanaukee et al., Acetaldehyde Modified Hemoglobin as a Marker of Alcohol Consumption, J Clin Med 1992; 120:42–7.

Sillanaukee et al., Effect of Acetaldehyde on Hemoglobin, Alcohol 8(5) 377–381, 1991.

Sillanaukee and Koivula, Detection of a New Acetaldehyde–Induced Hemoglobin Fraction, Alcohol Clin Exp Res 1990; 14: 842–846.

Bisse and Wieland, High–Performance Liquid Chromatographic Separation of Human Haemoglobins, J. Chrom, 434 (1988) 95–110.

Willard et al. "Instrumental Methods of Analysis" 1981 pp. 495–501.

*Primary Examiner*—Donald E Czaja
*Assistant Examiner*—Lien Tran
*Attorney, Agent, or Firm*—Thompson Hine & Flory

[57] ABSTRACT

A chromatographic method used to detect chronic alcohol usage and alcoholism and to monitor alcohol rehabilitation treatment; the method provides improved resolution of the Hb $A_{1-AcH}$ peak from the contiguous Hb $A_{1c}$ peak by means of a polyaspartic acid chromatographic column and a non-linear buffer gradient; the resulting Hb $A_{1-AcH}$ peak is then evaluated to determine chronic alcohol usage which is indicative of alcoholism and which can be used to monitor alcohol rehabilitation treatment.

7 Claims, 3 Drawing Sheets

SEPARATION OF ACETALDEHYDE - INDUCED HEMOGLOBIN (HB $A_{1-ACH}$)

FIELD OF THE INVENTION

The invention relates to a procedure whereby one acetaldehyde adduct of hemoglobin, commonly designated as Hb $A_{1-Ach}$, can be separated from contiguous hemoglobin peaks (Hb Pre-$A_{1c}$ and Hb $A_{1c}$) during the process of liquid chromatography and used to diagnose chronic alcohol use, alcoholism or to monitor alchoholism treatment.

BACKGROUND OF THE INVENTION

Alcohol abuse has become a problem of epidemic proportions in industrialized countries. The accepted medical treatment includes counselling and behavior modification. However, other than asking for a direct admission from a patient, few tests exist to determine whether that patient is an alcoholic or a chronic alcohol user.

Many of the tests which have been developed rely upon biochemical markers which reflect changes in particular liver enzymes which indicate hepatic damage or abnormal hematological tests which are impaired by prolonged elevation in blood alcohol levels. The value of these tests is measured by their sensitivity (i.e., the percent of alcoholics showing a positive test) and specificity (i.e., the percent of non-alcoholics showing a negative test). The sensitivity and specificity of these tests is not high because other forms of liver injury or abnormalities other than alcoholism, influence the biological markers. Because of the influence of these other factors, tests based upon a marker directly derived from a metabolite of ethanol, such as acetaldehyde, which is not influenced by conditions unrelated to alcohol abuse would have advantages.

Acetaldehyde (AcH), the primary metabolite of ethanol, has been known to bind covalently to form stable adducts with many proteins including hemoglobin (Stevens, V. J. et al., J. Clin. Invest. 67:361–69, 1981) and it has been proposed to use these adducts as a biological marker for alcoholism and chronic alcohol use. Acetaldehyde adducts can be detected in blood from volunteers who have consumed alcohol (Niemelä, O, et al., Alcoholism: Clin. Exp. Res. 14:838–41, 1990) and in the serum of alcoholic patients (Lin, RC, et al., Alcoholism: Clin. Exp. Res. 14:438–43, 1990) using various antibodies developed against protein-AcH adducts in enzyme-linked immunosorbent assays (ELISA). Unfortunately, these assays lack specificity owing to difficulties in the selection of specific Ach-protein adducts for development of antibody formation.

In 1984, Homaidan reported that acetaldehyde-hemoglobin adducts were an unreliable marker of alcohol abuse (Homaidan, F. et al., Clin. Chem. 30:480–82, 1984). Homaidan was unable to detect differences between alcoholics and social drinkers in the amounts of so-called "fast hemoglobins" (variants of $HbA_0$) produced by acetylation by acetaldehyde or glycosylation by sugars when measured by cation-exchange chromatography or by agar gel electrophoresis.

The separation of hemoglobin fractions by high pressure liquid chromatography (HPLC), offers markedly improved resolution of hemoglobin A variants when compared to previous methods of iso-electric focusing and ion-exchange chromatography. Huisman, T. H. J. et al., J. Lab. Clin. Med. 102:163–173, 1983, may represent the earliest detection by HPLC of the Hb $A_{1-AcH}$ complex as an unidentified minor Hb which cochromatographed with Hb $A_{1c}$ in the blood of alcoholics.

Sillanaukee and Koivula (Alcoholism: Clin. Exp. Res. 4:842–46, 1990) found that AcH induces an increase in Hb $A_{1-AcH}$ which is one of the faster eluting hemoglobin A variants when separated by HPLC. They proposed its use as a diagnostic marker in alcoholism (as a ratio of HB $A_{1-AcH}$/HB $A_{1c}$) and as an indicator of heavy drinking (Sillanaukee, P. et al., Alcohol & Alcoholism 26:519–25, 1991 and Sillanaukee et al., J. Lab. Clin. Med. 120:42–47, 1992). However, difficulties have been encountered in using the Hb $A_{1-AcH}$ adduct as a biological indicator of alcohol abuse. The method used by Sillanaukee, inadequately resolves the Hb $A_{1-AcH}$ peak from the contiguous Hb $A_{1c}$ complex. This seriously compromises the ability of the analysis to diagnose chronic alcohol usage. The Hb $A_{1c}$ complex is associated with a number of nonalcoholic conditions including diabetes and, hence, is elevated in many non-heavy drinking subjects such that if the Hb $A_{1-AcH}$ peak does not adequately resolve from the Hb $A_{1-Ach}$ complex, the Hb $A_{1-AcH}$ peak is dwarfed by the much larger the contiguous Hb $A_{1c}$ peak and integration of the Hb $A_{1-AcH}$ peak is prevented.

SUMMARY OF THE INVENTION

The present invention provides a method for achieving improved resolution of hemoglobin peaks and particularly the Hb $A_{1-AcH}$ peak and thereby provides improved quantitation of AcH adducts of Hb and a more reliable test useful in the diagnosis of alcohol abuse and monitoring alcoholism treatment for resumed drinking. This invention solves the problems in the Sillanaukee assay by offering an improved resolution of the Hb $A_{1-AcH}$ peak from the contiguous Hb $A_{1c}$ peak. In accordance with the invention, by using a polyaspartic acid chromatographic column and a non-linear buffer gradient elution of the Hb $A_{1c}$ complex can be controlled such that this complex is a reliable marker for alcohol abuse. This invention solves the Homaidian problem by providing a method by which clinicians can use acetaldehyde-hemoglobin adducts as an indicator of alcohol consumption. This invention is more reliable than previous methods because the Hb $A_{1-AcH}$ peak is measured independently of the Hb $A_{1c}$ peak and the Hb $A_{1-AcH}$ peak is directly tied to alcohol consumption. Finally, this method can detect changes in hemoglobin peaks using AcH concentrations in the micromolar range which corresponds to AcH blood levels during heavy alcohol consumption.

DETAILED DESCRIPTION OF THE INVENTION

Figure 1:
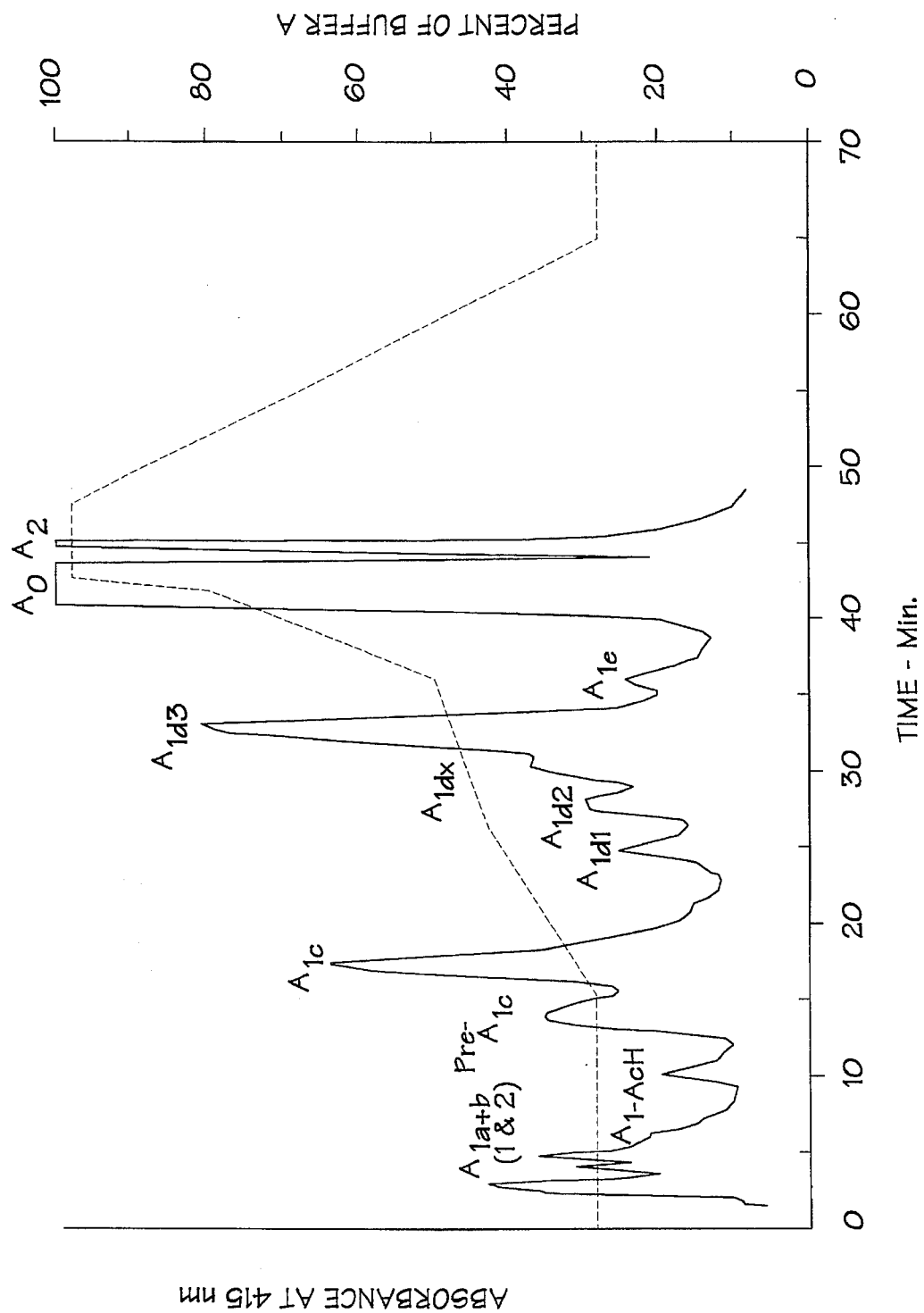
FIG. 1 is a graph of absorbance versus time at 415 nm and the Buffer A gradient versus time for a chromatogram of a hemosylate prepared from the blood sample of one alcoholic subject admitted with a blood alcohol level (BAL) greater than 200 mg/dL.

FIG. 1 is a liquid chromatograph of a blood sample for a patient, diagnosed as an alcoholic, in which hemoglobin peaks have been identified showing the resolution of the Hb $A_{1-AcH}$ from the Hb $A_{1c}$ complex. All references to hemoglobin peaks, e.g. Hb $A_{1-AcH}$ and Hb $A_{1c}$, herein, are made with reference to the labelled peaks in FIG. 1.

Figure 2:
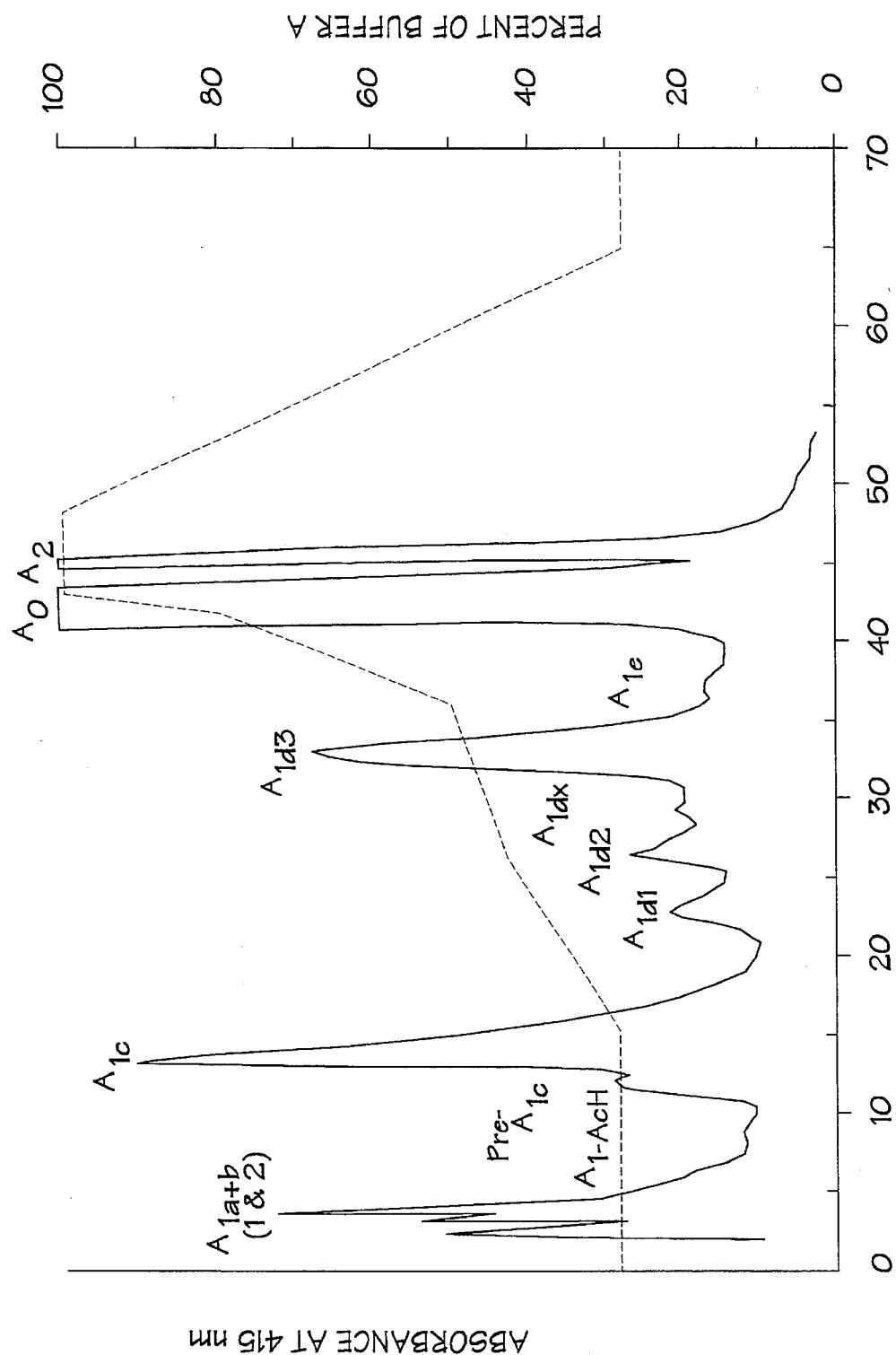
FIG. 2 is a graph of absorbance versus time at 415 nm and the buffer gradient for a chromatogram of a hemosylate prepared from a control blood sample.
Figure 3:
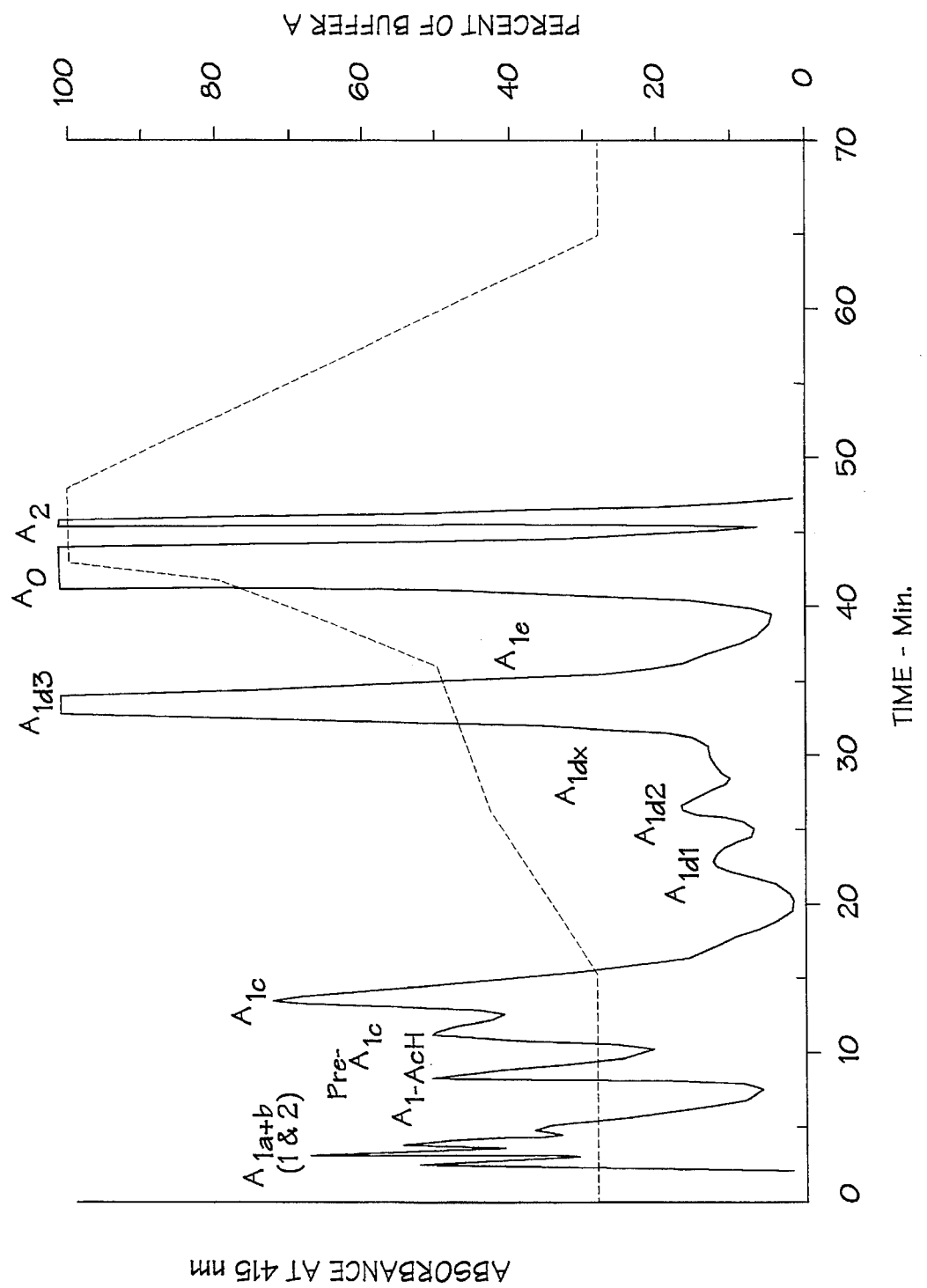
FIG. 3 is a graph of absorbance versus time at 415 nm for a chromatogram of a hemosylate prepared from a control blood sample of FIG. 2 after incubation of the sample with 300 μM of acetaldehyde (AcH) for 15 min.

FIGS. 2 and 3 show a comparison of chromatogram from a non-drinking control subject (FIG. 2) and the same hemosylate after incubation at 37° C. for 15 min. with 300 μM AcH (FIG. 3). As can be seen, the addition of AcH causes a marked increase in the peak designated as Hb $A_{1-AcH}$. Increases in the relative percentage of hemoglobins can be detected at 2 peaks within the Hb $A_{1a+b}$ cluster as well as the Hb pre-$A_{1c}$ peak and the Hb $A_{1d3}$ peak. Corresponding decreases are seen in the Hb $A_{1c}$ and Hb $A_0$ peaks after incubation with Ach.

In accordance with the invention, blood is collected from the subject to be tested and washed twice with a sodium chloride solution. The blood is then centrifuged to separate the red blood cells from the plasma. In order to eliminate the effects of short-term drinking on the test and thereby reduce the incidence of false positives, it is necessary to remove labile Schiff bases from the sample. These bases are unstable Hb AcH complexes which are formed in the blood and associated with the metabolism of alcohol. These bases can be found in the blood of any subject which has consumed alcohol and are not associated with chronic alcohol usage. While not desiring to be bound, these complexes are believed to be held together by weak intermolecular forces. With chronic excessive use of alcohol, the bonds forming these complexes are believed to convert to stronger, less labile, possibly covalent bonds. The labile bases can be removed by incubating the red blood cells in a sodium acetate buffer and then centrifuging to sediment the red blood cells. Incubation of AcH-incubated hemosylates with sodium acetate buffer for 30 min. at 37° C. completely removes the Hb pre-$A_{1c}$ as expected for unstable Schiff bases as shown in Table 1. This same treatment reduces the Hb $A_{1cH}$ and Hb $A_{1d3}$ peaks by approximately 50%, indicating that, at least under these conditions, some of the acetylated products represent reversibly bound Schiff bases.

TABLE 1

Effect of sodium acetate buffer removal of unstable Schiff base AcH-hemoglobin adducts after incubation with 1000 μM AcH for 30 min. (% of Total peak area - avg. of 3 detm'ns.)

| Hb Peak | With Na Acetate Buffer | Without Na Acetate Buffer |
| --- | --- | --- |
| Hb $A_{1a+b}(1)$ | 0.900 | 0.889 |
| Hb $A_{1a+b}(2)$ | 0 | 1.050 |
| Hb $A_{1-AcH}$ | 0.560 | 1.623 |
| Pre-Hb$A_{1c}$ | 0 | 1.078 |
| Hb $A_{1c}$ | 3.363 | 3.140 |
| Hb $A_{1d3}$ | 4.859 | 8.750 |
| Hb $A_0$ | 85.344 | 79.303 |

After removing the labile complex, the red blood cells are hemolyzed with an equal volume of water and 0.4 volumes of carbon tetrachloride, vortexing, and shaking. The sample is then centrifuged to separate the cellular debris from the hemoglobin in the supernatant. The concentration of the hemoglobin is determined by absorbency of the supernatant at 540 nanometers. The samples are then diluted with a buffer solution, frozen, and stored until ready for analysis.

Before injection onto the column, the samples are preferably filtered through a 0.2 micron filter. The HPLC column is washed with a mixture of buffer solutions. During the HPLC, a nonlinear buffer gradient is employed as described below. The effluent absorbency is typically monitored at 415 nanometers. Upon completion of the HPLC, the column is washed with Buffer A and recycled to the initial buffer ratio.

To diagnose alcohol abuse, chronic usage or alcoholism, the amount of Hb $A_{1-Ach}$ complex as a percentage of the total hemoglobin A complex is measured. Studies have shown that totally abstaining non-alcoholic drinkers typically have Hb $A_{1-Ach}$ mean levels of about 0.058%±0.056% S.D. Adding two standard deviations to the mean, a level of 0.176% or more of Hb $A_{1-Ach}$ complex is considered a reliable threshold indication of chronic alcohol use. Typically alcoholics will exhibit levels of Hb $A_{1-AcH}$ complex of about 0.2% or greater.

The invention is illustrated in more detail by the following non-limiting examples.

Examples

Sample Preparation:

Human blood is collected in an EDTA Vacutainer. The sample is then washed twice with 0.9% sodium chloride solution. To separate the red blood cells from the plasma, the sample is centrifuged for ten minutes at 1000×G. Schiff bases are removed by first incubating the red blood cells for thirty minutes at 37° C. with a sodium acetate buffer having a pH =5.5 and then centrifuging the samples at 2,000×G for ten minutes to sediment the red blood cells. The sodium acetate buffer consisted of 0.05M sodium acetate trihydrate and 0.11M sodium chloride adjusted to pH =5.5 with 2M acetate acid. The red blood cells are then hemolyzed by adding an equal volume of water and 0.4 volumes of carbon tetrachloride, vortexing the solution for five seconds, and shaking for 15 minutes. To separate cellular debris from hemoglobin in the supernatant, the samples are centrifuged at 2,000×G for 15 minutes. The concentration of hemoglobin in the samples can be determined by the absorbency of the supernatant, diluted 1:100, at a wavelength of 540 nanometers.

The samples are diluted to 2 mg/ml with a third buffer (Buffer B). This buffer consisted of 3 mM Bis Tris, 3 mM ammonium acetate, and 1.5 mM potassium cyanide, adjusted to pH =6.6 with 20% acetic acid. The diluted samples were frozen at −30° C. , and stored until ready for chromatography. Before injection onto the column, all samples are filtered through a two micron filter.

HPLC of samples:

Separation of the hemoglobins was accomplished using a polyCAT A column (a cation exchange column packed with polyaspartic acid covalently bonded to silica) 200 mm ×6 mm in diameter. The packing consisted of 5 μm particles with a 1,000 angstrom pore size. The column is protected by a guard cartridge having the same packing. The column and the guard cartridge were purchased from PolyLC Inc. of Columbia, Md.

The flow rate of the column is 2 ml/minute at a pressure of 100 atmospheres. The effluent absorbency is monitored at 415 nanometers using a Varian Star 9010 HPLC with a Varian variable wavelength detector connected to a Hewlett Packard HP 339A integrator. The integrations are preformed at an attenuation of 2↑=0 with a chart speed of 0.3 cm/min. and a peak width =0.64 min.

Before each run the column is conditioned with a 28:72 mixture of Buffer A:Buffer B. Buffer A consisted of 35 mM bis[2-hydroxyethyl]amino-tris-[hydroxymethyl] methane (Bis Tris), 16.85 mM ammonium acetate, 90 mM sodium acetate, and 1.5 mM potassium cyanide, adjusted to pH =6.8 with 20% acetic acid. From time (T) T=0 to T=15 minutes, the A:B buffer ratio is maintained at 28:72. From T=15 to T=43 minutes, the buffer ratio is increased to 100:0 using a nonlinear gradient as shown in FIG. 1 and in the following table:

| Time | % Buffer A | % Buffer B |
| --- | --- | --- |
| T = 0 to T = 15 | 28 | 72 |
| T = 15 to T = 26 | 43 | 57 |
| T = 26 to T = 36 | 50 | 50 |
| T = 36 to T = 42 | 80 | 20 |
| T = 42 to T = 43 | 100 | 0 |

After the chromatogram is completed, the column is washed with 100% Buffer A for five minutes and then recycled to 28:72 before the next run.

Having described the invention in detail and by reference to preferred embodiments thereof, it will be apparent that modifications and variations are possible without departing from the scope of the invention defined in the appended claims.

What is claimed is:

1. A method for detecting alcoholism or heavy drinking or monitoring alcoholism treatment in human subjects which comprises the steps of:

collecting a sample of whole blood from a human subject;

separating the red blood cells from the plasma in the whole blood sample;

hemolyzing the red blood cells;

providing a first buffer comprising 35 mM Bis Tris, 16.85 mM ammonium acetate, 90 mM sodium acetate and 1.5 mM potassium cyanide adjusted to pH =6.8 with 20% acetic acid;

providing a second buffer comprising 36 mM Bis Tris, 3 mM ammonium acetate and 1.5 mM potassium cyanide adjusted to pH =6.6 with 20% acetic acid;

providing a high pressure liquid chromatographic system employing a cation exchange stationary phase consisting of polyaspartic acid covalently attached to silica;

introducing the first buffer and the second buffer into the high pressure liquid chromatographic system in accordance with the following table:

| Time (min.) | % First Buffer | % Second Buffer |
| --- | --- | --- |
| T = 0 to T = 15 | 28 | 72 |
| T = 15 to T = 26 | 43 | 57 |
| T = 26 to T = 36 | 50 | 50 |
| T = 36 to T = 42 | 80 | 20 |
| T = 42 to T = 43 | 100 | 0 | analyzing a sample of the hemoglobin in the high pressure liquid chromatographic system whereby a chromatogram is obtained in which an Hb $A_{1-AcH}$ peak is resolved; and evaluating the Hb $A_{1-AcH}$ peak to diagnose alcohol usage.

2. The method according to claim 1 wherein the red blood cells are treated to remove any unstable Schiff bases which may be present therein.

3. The method according to claim 2 wherein said sample of hemoglobin is analyzed in a variable wavelength ultraviolet detector at about 415 nanometers.

4. The method according to claim 3 wherein the step of analyzing the sample further includes conditioning the high pressure liquid chromatographic column prior to a run for five minutes with 28% first buffer: 72% second buffer.

5. The method according to claim 2 wherein the step of removing unstable Schiff bases from the red blood cells includes incubating the red blood cells for 30 minutes at 37° C. with a sodium acetate buffer consisting of 0.05M sodium acetate trihydrate and 0.11M sodium chloride adjusted to pH 5.5 with 2M acetic acid and then centrifuging for 10 minutes at 2,000×G to sediment the red blood cells.

6. The method according to claim 2 wherein the step of evaluating the Hb $A_{1-AcH}$ peak includes integrating the Hb $A_{1-AcH}$ peak and calculating the ratio of the Hb $A_{1-AcH}$ complex to total hemoglobin A complex.

7. The method according to claim 4 wherein a ratio in excess of about 0.176% constitutes a positive diagnosis of heavy alcohol usage.

\* \* \* \* \*